United States Patent [19]

Eisenhardt, Jr. et al.

[11] 4,243,605

[45] Jan. 6, 1981

[54] NOVEL ISOCYANATES

[75] Inventors: William A. Eisenhardt, Jr., Yorktown Heights; Eddie Hedaya, White Plains; Spyros Theodoropulos, Yorktown Heights, all of N.Y.

[73] Assignee: Union Carbide Corporation, New York, N.Y.

[21] Appl. No.: 921,809

[22] Filed: Jul. 3, 1978

Related U.S. Application Data

[62] Division of Ser. No. 687,149, May 17, 1976, Pat. No. 4,115,539.

[51] Int. Cl.$^2$ ............................................... C07F 7/18
[52] U.S. Cl. .................................................... 556/414
[58] Field of Search ................................. 260/448.8 R

[56] References Cited

U.S. PATENT DOCUMENTS 4,031,121  6/1977  Gervase ..................... 260/448.8 R

*Primary Examiner*—Paul F. Shaver
*Attorney, Agent, or Firm*—Harrie M. Humphreys

[57] ABSTRACT

Novel isocyanates such as, for example, blocked L-tyrosine methyl ester isocyanate, are reacted with compounds of biological, clinical interest or the like such as, for example, digoxin, to form derivatives receptive to tagging, as by radioliabeling. The tagged derivatives may then be employed to determine the presence of the compound of interest in nanomolar or even picomolar amounts by using clinical analysis techniques such as radioimmunoassay.

4 Claims, 1 Drawing Figure

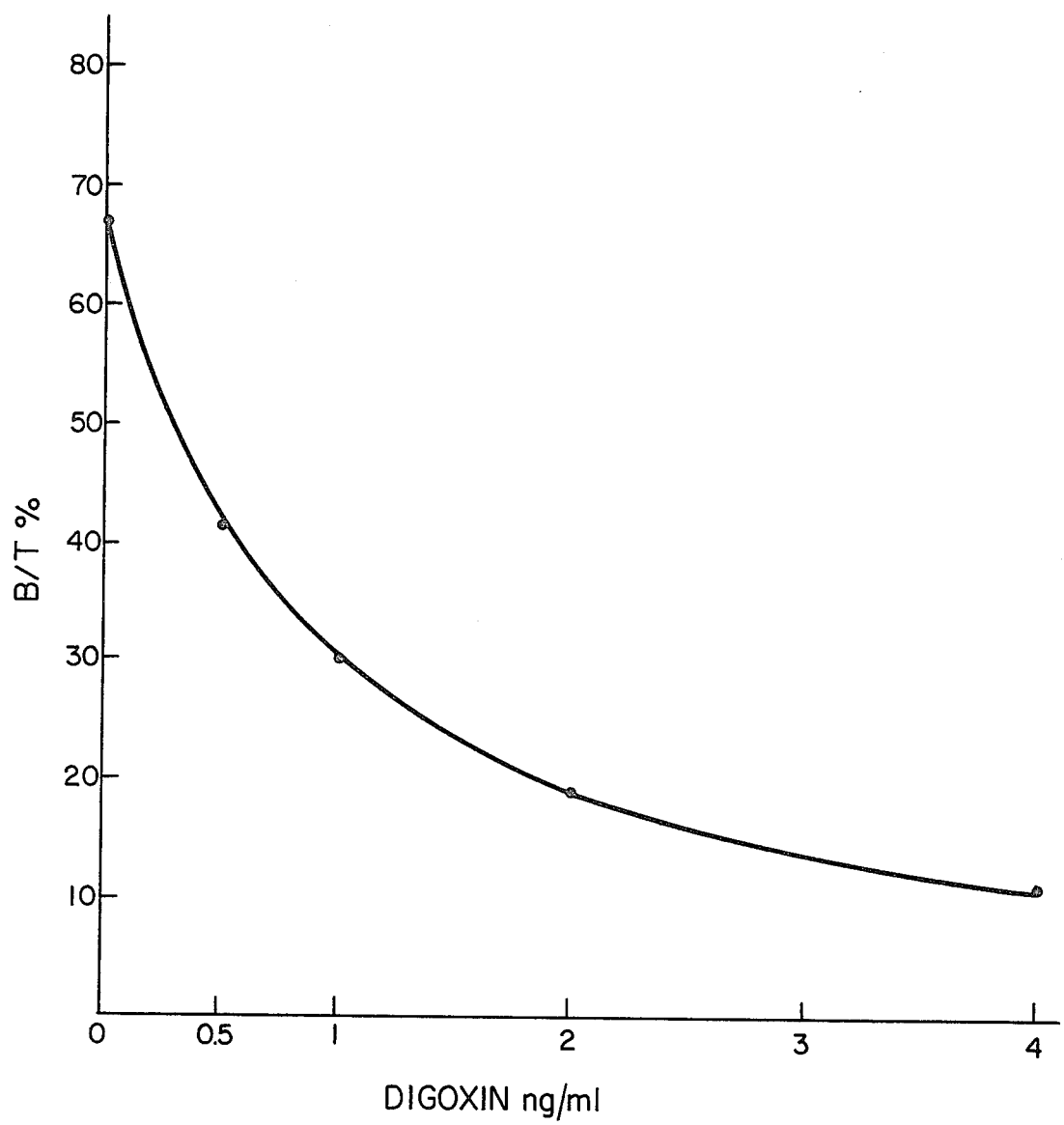

NOVEL ISOCYANATES

This application is a divisional application of U.S. Ser. No. 687,149 entitled, "Analytical or Clinical Derivatives, Tagged Derivatives and Methods of Analysis Using Such Derivatives", by W. A. Eisenhardt, Jr. et al., filed May 17, 1976, now U.S. Pat. No. 4,115,539.

BACKGROUND OF THE INVENTION

This invention relates to the analysis of various compounds in biological fluids or the like and, more particularly, to novel isocyanates capable of reacting with the compounds of interest to form derivatives receptive to tagging, as by radiolabeling, and to methods of analysis using such tagged derivatives.

For a variety of clinical purposes such as, for example, monitoring dosage schedules, monitoring hormone levels, checking for recent ingestion or following pharmacological dynamics of bioavailability, absorption, degradation or excretion, it is of great advantage to measure the concentration of various drugs or the like to the nanomolar or even picomolar level. As is known, radioimmunoassay can accomplish analyses of this type. To carry out an analysis, an acceptable kit or system must include an antiserum, a standard of the compound to be measured, the radiolabeled derivative of the compound to be measured, a buffering agent or agents and, often, a displacing agent. As is known, the antiserum is produced by bleeding animals which have been immunized by innoculation, for example, with the hapten-protein conjugate (immunogen) corresponding to the compound to be measured (typically termed "antigen").

As is known, in general, the technique of radioimmunoassay measures the competition between radioactively labeled antigen and unlabeled antigen for binding sites on the antibody in the antiserum. By adding to the antiserum known amounts of the antigen to be assayed and a radiolabeled analog, a dose-response curve for bound or free antigen vs. concentration of antigen is constructed. After this immunocalibration has been carried out, unknown concentrations can then be compared to the standard does-response curve for assay. Crucial to this type assay is the existence of radioactive antigens which compete effectively with non-radioactive antigens. Accordingly, in order to obtain the maximum precision, accuracy, sensitivity, specificity and reproducibility of the assay, purified, well-characterized synthetic radioactive antigens are required. The sensitivity refers to the ability of the assay technique to respond to minimal concentrations of the antigen (viz., the hormone, drug or the like being assayed). Maximal sensitivity is attained when the concentration of free, radiolabeled antigen is negligible, and the concentration of unlabeled antigen approaches zero. When the synthetic, radiolabeled antigen is pure and closely matches in conformation the antigen whose analysis is sought, radioimmunassay is potentially of the highest sensitivity and specificity.

Synthesizing satisfactory radioactive antigens thus involves certain guidelines. Pure reagents with a minimum concentration of by-products should be utilized. In addition, high-yield, gentle reactions which do not rearrange the antigen or hapten are desired as are reactions which cause only minimal structural alterations of the hapten or antigen. Still further, it is desirable to use derivatizing chemistry that minimizes differences in affinity toward the binding reagent, e.g.—antibody, of radiotracer and native hapten or antigen so that effective competitive assay is possible.

Tagging of the hapten or antigen being assayed can be achieved, as is known, with $^{14}C$ or $^3H$. However, analyses involving haptens or antigens tagged by this technique are slow and tedious and can generally only be accomplished by liquid scintillation methods. It is accordingly desirable to radiolabel by tagging with an iodine radioisotope such as, for example, $^{125}I$. However, most compounds which are of interest cannot be labeled by this technique and must accordingly be reacted with an iodine-accepting group. Aromatic rings and some heterocyclic rings, especially those activated for facile substitution, are thus preferred constituents for coupling two compounds to provide derivatives receptive to iodine labeling. For this reason, tyrosine methyl ester and tyramine, both containing an activating phenolic hydroxyl group, have been used to provide derivatives which can later be radiolabeled.

One of the conventional methods previously utilized to prepare tagged steriods involves the initial formation of an intermediate adduct by treatment of the steroid with a chloroformate or succinyl, maloyl, fumaroyl or phthaloyl ester or anhydride followed by a subsequent reaction with the iodine acceptor. This approach is described in Oliver et al., *J. Clinical Investigation,* Vol. 47, p. 1035 (1968) wherein 3-0-succinyldigitoxigenin-tyrosine methyl ester and the corresponding $^{125}I$ derivative were prepared for use in the radioimmunoassay of digitoxin in humans. A further approach of this type is shown in U.S. Pat. No. 3,810,866 wherein digitoxigenin is linked to derivatives of tyrosine, 4-hydroxyphenylglycine, 3-hydroxytryptophane, tryptophane and histidine by means of a succinyl, maloyl, fumaroyl or phthaloyl group.

The preparation of such derivatives can take up to several months.

A further technique is described in German application No. 2,331,922, dated Jan. 10, 1974. In this procedure, there is shown derivatives of 14 different cardiac glycosides which are radiolabeled by first opening the terminal digitoxose ring and oxidizing to the dialdehyde with periodate. The dialdehyde is then coupled with a reagent such as L-tyrosine methyl ester hydrochloride. The resulting adduct is then reduced with sodium borohydride to reduce the remaining hydroxyl groups on the end sugar ring and, incidentally, to saponify the ester to the acid. This adduct can then be radioiodinated on the aromatic ring. This method tends to be cumbersome, subject to by-products at the various intermediate stages and further employs relatively strong reagents.

Yet another technique is shown in South African application No. 73-8312, dated Oct. 16, 1973. This coupling technique may be employed with steroidal ketons such as testosterone by first forming the carboxymethyl oxime. The iodine acceptor such as, for example, tyrosine methyl ester, is then caused to reac with a typical carbodiimide such as N,N-dicyclohexylcarbo..iimide in the presence of triethylamine in methylene cn.oride to produce the tyrosine methyl ester amide of the original 0-carboxymethyloxime.

It is accordingly an object of the present invention to provide novel isocyanates which may be readily coupled to compounds of clinical interest to provide derivatives which are receptive to tagging, as by radiolabeling.

A further object provides novel carbamate and urea derivatives of compounds of biological, clinical or other interest. A related and more specific object lies in the provision of such derivatives which are receptive to radiolabeling.

A still further object is to provide coupling reagents capable of forming carbamates or ureas useful for joining molecules or clinical interest to substrates of interest such as, for example, proteins, enzymes, polypeptides, glass beads, carbohydrates, plastic articles and the like.

A still further object provides a method of radioassay using as reagents the radiolabeled carbamates or ureas described herein.

Yet another object of this invention lies in the provision of novel coupling agents which form adducts with compounds of clinical interest by a facile, gentle chemical reaction.

Another object is to provide the formation of adducts between the novel coupling agents of this invention and the compound of clinical or other interest which is characterized by synthetic breadth, ease of reaction, procedural simplicity and relative freedom from by-products.

A still further object of this invention provides labeled derivatives which improve the reliability of radioimmunoassay, immunoassay and nonimmune-based techniques utilizing, for example, competitive binding agents.

Other objects and advantages of the present invention will become apparent from the following detailed description and from the sole FIGURE which depicts a typical dose-response curve obtained utilizing, as the radiomarker, a radioiodinated digoxin derivative of the present invention.

While the invention is susceptible to various modifications and alternative forms, there will herein be described in detail the preferred embodiments. It is to be understood, however, that it is not intended to limit the invention to the specific forms disclosed. On the contrary, it is intended to cover all modifications and alternative forms falling within the spirit and scope of the invention as expressed in the appended claims. For example, while the present invention will be described in connection with assays carried out by radioimmunoassay techniques, it should be appreciated that the present invention is equally applicable to use in any type of assay involving similar principles. Still further, while most proteins and many peptides can be radioiodinated without coupling an iodine acceptor thereto, it may be advantageous to employ the novel coupling agents of the present invention to add additional iodine-accepting sites to the protein or peptide to allow for greater specific activity. Additionally, in cases where the strong oxidizing and reducing conditions frequently employed in radioiodination procedures may be detrimental to the structure or properties of the proteins, it may be desirable to pre-radioiodinate the novel coupling agents of the present invention, which then may be subsequently reacted, after purification, if desired, with the protein or peptide under chemically mild conditions. Similar considerations may also apply to the larger entities containing proteins such as viruses, bacteria, cells and the like.

SUMMARY OF THE INVENTION

In general, the present invention is predicated on the discovery that novel isocyanates may be made from compounds containing moieties known to be receptive to tagging, as by radiolabeling, such as, for example, tyramine and tyrosine by a technique involving inherent blocking of the functional, reactive group other than the isocyanato radical so as to allow preparation of derivatives of such isocyanates with compounds of clinical or other interest. The resulting derivatives may then, after suitable deblocking, be readily tagged and used in techniques such as radioimmunoassay to provide reliable, precise, sensitive assays.

DETAILED DESCRIPTION OF THE INVENTION AND PREFERRED EMBODIMENTS

In accordance with the present invention, novel isocyanates are provided whcih contain a block moiety functioning, after deblocking, to provide a reactive group receptive to either tagging or coupling to a substrate of interest. The utilization of the novel isocyanates provides distinct advantages over prior techniques since the reactions forming the derivatives are straightforward, gentle in nature and entail little alteration of the structure of the compound of interest.

The blocked functional, reactive group or groups of the isocyanate will be dependent upon the intended application. Thus when the isocyanate is to be employed to ultimately form a radioiodinated adduct with the compound of clinical or other interest, the functional, reactive group should, of course, be receptive to radioiodination or activate a moiety that is radioiodinatable. For this purpose, it is preferred to utilize an isocyanate based on either tyramine or L-tyrosine methyl ester. In these species, as is known, the p-hydroxyl group activates the ring, allowing radioiodination.

However, if desired, the isocyanate employed can, from the functional standpoint, by any isocyanate containing a moiety or reactive group receptive to radioiodination. It is accordingly within the scope of the present invention to utilize isocyanates based on unsaturated compounds such as olefins, e.g. - allyl amine. Acetylenes may perhaps also be used. A further group of useful isocyanates may be derived from hydroxyl-containing amines such as, for example, catecholamines. Further useful species are disclosed in French pat. no. 2,266,888, the isocyanate thus containing a moiety having the following formula:

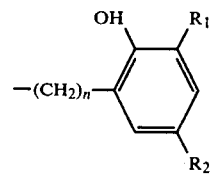

wherein n is an integer of from 1 to 5 and $R_1$ and $R_2$ may be methyl, ethyl, methoxy, ethoxy, or a halogen. Other useful species include isocyanates derived from 4-hydroxyphenylglycine, 5-hydroxytryptophan, tryptophan and histidine. Still further useful isocyanates may be derived from radioiodinatable heterocyclics such as, for example, histamine, imidazoles, indoles, cytosine, pyrimidine, adenine and adenosine.

For other applications, it may be desirable to utilize isocyanates which are capable of absorbing light, emitting absorbed light (e.g.—fluorescence or phosphorescence) or lasing. Isocyanates of this type can be prepared by two methods. Thus, an isocyanate can be prepared with a moiety which is itself capable of absorbing light (e.g.—tyramine), emitting absorbed light (e.g.—pyrene or napthalene) or lasing (e.g.—rhodamine 6G). Alternatively, where an isocyanate cannot be formed directly from the moiety, an isocyanate can be utilized which contains a group reactive with such moieties. In this connection, an illustrative example of a useful isocyanate can be derived from 1-trifluoroacetoamido-6-aminohexane. After reaction of the isocyanate and suitable deblocking, the isocyanate adduct can then be reacted with another moiety of interest. In some instances, even if an isocyanate can be formed the moiety, it may be desirable to first form an isocyanate which may subsequently be reacted with the moiety. As an example, this would be useful to allow further spacing of the moiety from the compound of interest which is reacted with the isocyanate.

Useful isocyanates can also be prepared from moieties capable of chelating with a metal ion which may or may not be radioactive. Representative examples include isocyanates derived from ethylenediaminetetraacetic acid or ethylenetriamine-pentacetic acid. It should be appreciated that the chelating groups should be suitably blocked so as to allow survival of the isocyanate preparation.

A further type of useful isocyanates may be derived from moieties containing a radionuclide. As an example, an isocyanate derived from $^{75}$Se - selenomethionine can be utilized.

Yet another type of isocyanates which may be employed can be derived from moieties capable of being detected by electron spin resonance spectroscopy. For example, a useful isocyanate can be derived from a moiety containing the radical:

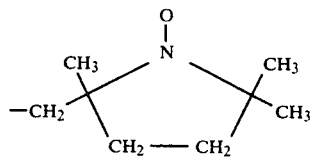

A further useful isocyanate containing a spin label moiety can be prepared using the free radical: 4-amino-2,2,6,6-tetramethylpiperidinooxy.

It is also within the scope of the present invention to employ isocyanates containing a moiety having a reactive group (other than the isocyanate group) which is capable of coupling the isocyanate to either a substrate of interest, typically insoluble, or to a compound of interest. Examples of substrates of interest include glass beads, dextrans, cellulose or various plastics. An example of an isocyanate with a suitable coupling moiety can be derived from Si(OEt)$_3$, wherein OEt represents an ethoxy radical. For coupling to an enzyme, virus, protein or a cell, suitable isocyanates can be derived from moieties containing —SH, —CO$_2$H or amino groups.

As will be appreciated, to allow the desired reactive group to survive the preparation of the isocyanate, it will typically be necessary to suitably block or protect the reactive group.

The isocyanates useful in this invention may be desirably prepared, according to the process described in the copending Hedaya et al. application described herein. In general, this involves forming the carbamic acid salt from the appropriate primary amine and then reacting to form the corresponding halosilylcarbamate, as the isocyanate precursor. The isocyanate is then formed by gently heating the halosilylcarbamate.

The formation of these isocyanates may be carried out at temperatures ranging from ambient to about 150° C., with lower temperatures in the range of from about 30° to about 60° C. being preferred to minimize side products. The reactions may be carried out in the presence of either a nonpolar solvent or a polar solvent such as, for example, a tertiary amine. More specific details of the process are described in the co-pending Hedaya et al. application, the disclosure of which is herein incorporated by reference.

Where blocking is needed to prevent polymerization, internal cyclization or other reactions forming undesirable by-products in the isocyanate synthesis, it is preferred to utilize the exchange process described in the Hedaya et al. application. This process inherently achieves blocking of the reactive, functional group of the amine. The formation of the corresponding blocked isocyanate from tyramine shows the blocking action. As illustrated hereinafter, the trialkylsilyl carbamate is formed by reaction of tyramine with carbon dioxide and a halosilane, the reaction being carried out in triethyl amine as the solvent:

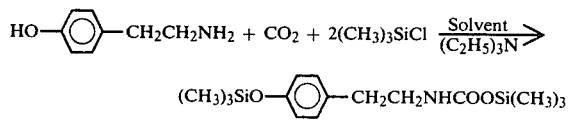

As can be seen, the formation of the trialkylsilyl carbamate results in blocking the hydroxyl group of the tyramine. The isocyanate is then formed by a trans-silylation reaction to form the halosilylcarbamate, followed by heating. This reaction sequence is set forth below:

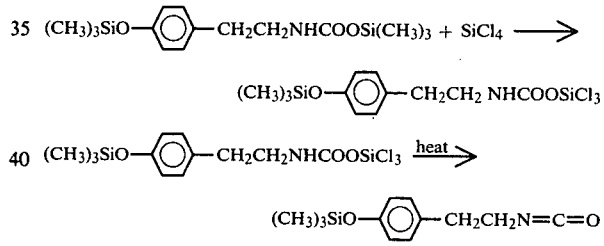

While, in the above illustration, the blocking radical is trimethylsiloxy, this is only by way of illustration. The particular siloxy blocking radical will depend upon the organic moiety of the silylating reagent used to form the silylcarbamate in the exchange process. The organic moiety may, conceptually, be any one which allows formation of the silylcarbamate, subsequent trans-silylation and conversion to the corresponding isocyanate.

Representative useful organic moieties include lower alkyls containing up to about ten carbon atoms such as dimethyl, methyl ethyl or methyl propyl. Alicyclic groups such as cyclopentyl, cyclohexyl or cycloheptyl may also be utilized but should contain about ten carbon atoms or less. Still further, aryl and alkaryl groups containing up to about ten carbon atoms may be used. Suitable examples include phenyl, tolyl and xylyl. In addition, aralkyl groups containing up to about ten carbon atoms such as benzyl may also be used. Any of these moieties may be substituted with one or more halogen atoms. It should be understood that the utilization of organic moieties having about ten carbons or less represents a preference rather than a limitation. Availability and cost will often dictate the particular silane utilized. A further consideration is the ease of conversion to the isocyanate, larger and bulkier organic molecules may provide a less facile conversion.

Accordingly, for isocyanates based upon tyramine, the structural formula is as follows:

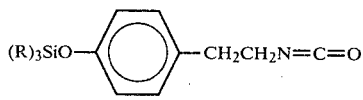

wherein R may be any of the organic moieties described in connection with the silylating reagent. Also, R can be a single moiety or mixed (e.g. - tert-butyldimethyl). For isocyanates based on L-tyrosine methyl ester, the corresponding structural formula is:

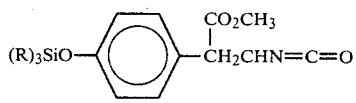

R being defined as before. Similarly, for isocyanates derived from ethanolamine, the structural formula is:

As will be appreciated, when reagents of tin, germanium, titanium, phosphorus or sulfur are substituted for the silane, the silicon will be similarly replaced in the blocking radical.

While in most cases, as has been discussed with tyramine, the use of the exchange process will provide adequate blocking, there are situations where this type of blocking may prove inadequate. For example, where an amino radical is to be blocked, this can be carried out by the exchange process; however, when the resulting isocyanate is reacted with the compound of clinical or other interest, premature deblocking (e.g.—as by hydrolysis) may occur, causing undesirable side reactions. This may perhaps be avoided by selection of silylating agents which will provide relatively bulky blocking groups, or by modifying reaction conditions. Alternatively, other known blocking techniques can be employed. For example, the reactive group could be blocked by utilizing trifluoroacetoamido radicals.

The isocyanates may then be reacted with any compound of interest capable, of course, of reacting with an isocyanato radical. Typically, for example, any compound containing, in the classical sense, an active hydrogen group may be coupled to the isocyanates, e.g., any compound containing a hydroxyl, amino, sulfhydryl or carboxyl group may be utilized. As is known, a wide number of proteins, amino acids, polypeptides, enzymes, steroids, drugs, nicotine derivatives, pesticides, various natural products, plant and animal hormones, viruses, polyamines, bacterial cells and other metabolites contain groups reactive with isocyanato radicals. Specific examples of compounds of clinical or other interest include angiotensin I and II, digoxin, digitoxin, digoxigenin, dihydrotestosterone, testosterone, aldosterone, cortisol, estrone, estradiol, estriol, gentamicin, penicillin, theophylline and 11α-hydroxyprogesterone.

It should also be appreciated that the present invention may also be utilized in connection with compounds of interest not containing a radical reactive with isocyanato radicals. This requires modifying the compound to incorporate such a reactive radical. As an example, nicotine can be utilized by first preparing 6-aminonicotine and then reacting with the desired isocyanate. The resulting adduct is a suitable analog for use in assaying nicotine.

The isocyanate-compound of interest adduct or derivative may be prepared utilizing, in general, known process conditions for the reaction of isocyanates. It is thus suitable, for example, to prepare the adduct by reaction in a solvent (if desired) at a temperature, ranging from ambient to about 150° C. Also, if desired, any of the several types of catalysts known to be useful in forming urethanes can be employed. As illustrative examples, useful types of catalysts include tertiary amones, salts or organic acids with a variety of metals such as alkali metals, and the like. Representative examples of useful solvents include pyridine, formamide, tetrahydrofuran, triethylamine, dimethylformamide, ethers, methylene chloride and the like, with pyridine being preferred.

The amount of solvent (if used) may vary as desired, often being determined by the purpose in using it in the first place. The relative amounts of reactants employed can likewise be varied as desired, and a slight excess of one of the reactants does not result in any adverse effects. Use of one of the reactants in less than a stoichiometric amount will, as could be expected, tend to decrease yields.

As will be appreciated, the conditions selected should be such as to insure that the structure of the compound of interest will not be degraded or otherwise adversely affected. For this reason, it is preferred to utilize as mild conditions as possible.

Many compounds of interest contain more than one radical reactive with isocyanato radicals. This can thus result in the formation of more than one specie. This can be minimized, and even avoided, by utilizing particular techniques. To this end, and in accordance with one aspect of the present invention, the reaction can be photoassisted. As is known, to allow preparation of urethanes which cannot be synthesized by other techniques, the reaction can be carried out in carbon tetrachloride with ferrocene.

For example, digoxin possesses six hydroxyl groups. Prior work suggests that the hydroxyl group on the 15' carbon atom is the most reactive, followed by the hydroxyl group on the 12 carbon atom. Without utilizing photoassistance, analysis of the reaction product of an isocyanate based on tyramine and digoxin is consistent with the presence of a mixture of digoxin carbamates, one specie having a urea linkage on the 15' carbon atom and the other specie having carbamate linkages on both the 15'- and the 12-carbon atoms. It has been discovered that the employment of a photoassisted reaction results only in a single specie consistent with a structure having a urea linkage on the 15' carbon atom.

Conceptually, a photoassisted reaction will likewise result in a single specie in cases where the reactive radicals of the compound of interest have differing relative reactivity of a magnitude similar to the hydroxyl groups in digoxin. More specifically, it is theorized that a photoassisted reaction sufficiently enhances the kinetics of the reaction with the most reactive group in relation to the reactivity of the other groups to allow formation of but a single specie.

Alternatively, providing a particular desired specie can also be accomplished by blocking of all the reactive groups and then selectively deblocking the desired site.

More specifically, using 17β-estradiol as an example, the two hydroxyl groups may each be blocked with a trimethylsilyl group by reaction with trimethylsilyl-N,N-dimethyl carbamate. To selectively remove the 3-trimethylsilyl group while leaving the 17-blocking group intact, the crude product can be selectively deblocked by using a known deblocking agent such as methanol and monitoring by nuclear magnetic resonance spectroscopy. This intermediate may then be reacted with the desired isocyanate, followed by deblocking of the unwanted reaction site.

Still further, if desired, where the reaction provides more than one specie, conventional separation techniques (e.g.—thin layer chromatography) may be employed to isolate the desired specie. Recrystallization or the like could also be employed.

As may be apparent from the above description, when it is necessary to block the reactive moiety of the isocyanate, it is preferred to form the desired adduct or derivative before deblocking. Deblocking, as is known, can suitably be accomplished by using various solvents such as aqueous methanol or the like. The deblocked reactive group may then be utilized to link the adduct with a substrate or other material of interest.

The isocyanates of this invention, containing a tagged moiety or a moiety receptive to tagging, may be advantageously utilized in any of the several known techniques involving competitive binding to quantitatively determine the presence of the compound of interest. The particular isocyanate used will, of course, be dependent upon the type of tagging required by the technique of choice. The technique selected will, in large part, be determined by the results required. Thus, for example, when used to determine the quantitative presence of a compound where maximum sensitivity is desired, as in the case generally with compounds of clinical or biological interest, it is preferred to use radioimmunoassay and a radioiodinated specie.

The radiolabeling of the isocyanate compound of interest derivative can be carried out by any of the several, known techniques. For example, radioiodinated derivatives may be prepared by one of the following methods: chloramine T method of Hunter-Greenwood, *Nature*, Vol. 194, p. 495 (1962); iodine monochloride method—Ceska, Grossmuller, and Lundkvist, *Acta Endocrinologia*, Vol. 64, p. 112–125 (1970); isotopic exchange method—Counsell, Ranade, Pocha, Willette and Diguilio, *J. Pharmaceut Sciences*, Vol. 57, p. 1657 (1968); and electrolytic iodination—Pennisi and Rosa, *J. Nuclear Biol. & Medicine*, Vol. 13, p. 64 (1964). It is desired, as the radioisotope, to employ $^{125}I$; however, other radioisotopes such as $^{123}I$, $^{129}I$ or $^{131}I$ may likewise be utilized.

The radiolabeled derivative may then be purified to isolate, if desired, a single specie using conventionally known techniques. For example, as is known in the art radioiodinated derivatives as formed may comprise a mixture of mono- and di-iodo species; and it may be useful to isolate a single specie.

The derivatives of the present invention are highly useful, well-characterized compounds which allow maximum precision, accuracy, sensitivity, specificity and reproducibility. Thus, due to the type of synthesis, pure reagents may be formed with a minimum concentration of by-products and the gentle reaction forming the derivatives minimizes the possibility of any rearrangement of the clinical compound being coupled with the isocyanates of the present invention. In addition, the derivatizing chemistry minimizes the differences in affinity toward the binding reagent of the radiotracer and the native hapten or antigen so that effective competitive assay is possble.

As is thus apparent, a further aspect of the present invention resides in a method of carrying out a competitive binding radioassay of a compound of interest utilizing the adducts of the present invention. This involves, as is known, preparing a calibration curve of disintegrations per unit time vs. concentration of the compound of interest. This may be prepared by a four step approach involving first reacting together: (1) a fixed numer of binding sites (for example antibody) specific for the compound of interest, (2) a fixed amount of the radiomarker or radiotracer and (3) varying amounts of pure standard reference compound. For each dilution of the standard in the initial step, the free species are separated from the bound species. Separation can be achieved by employing any suitable technique. A number of such techniques are known, e.g.—chromatoelectrophoresis or absorption and elution frame a small column of particulate charcoal, ion-exchange resin, cellulose or silica. Using a suitable radiation counter, the disintegrations per unit time in either the bound or free fraction of each reaction or dilution are determined. A standard curve of disintegrations per unit time vs. concentration of the pure reference compound can then be constructed.

The disintegrations per unit time for the compound of interest in the sample are then determined by subjecting the sample to competitive binding conditions. This is achieved using the same general steps as employed in constructing the standard curve. Thus, the same number of binding sites and the identical, fixed amount of radiomarker used to construct the standard curve are reacted together with the sample. After separation of the free species from the bound species, the radiation counter previously utilized is employed to determine the disintegrations per unit time for the same fraction used to construct the standard curve.

By employing the standard curve, the concentration of the compound of interest is the concentration corresponding to the disintegrations per unit time previously determined for the sample.

The following Examples are illustrative, but not in limitation, of the present invention.

DEFINITIONS

As used in the Examples appearing hereinafter, the following designations, symbols, terms and abbreviations have the indicated meanings:

| | |
|---|---|
| mol | mole |
| ml | milliliter |
| bp | boiling point |
| g | gram |
| ppm | parts per million |
| m | multiplet |
| q | quartet |
| J | coupling constant |
| t | triplet |
| d | doublet |
| s | singlet |
| Hz | hertz |
| eV | electron volts |
| $R_f$ | In thin layer chromatography, the proportion of the total length of climb of a solution that is reached by a spot characteristic of one of the |

-continued constituents present.

EXAMPLE 1

This Example illustrates the synthesis of an isocyanate from 2-(4'-hydroxyphenyl)ethylamine (triviallytyramine), which may be coupled to a compound of clinical interest to introduce a moiety capable of being radioiodinated after deblocking.

Into a 250 ml, three-necked flask fitted with a reflux condenser, gas inlet tube and magnetic stirrer and kept under a positive pressure of dry nitrogen, there was charged 100 ml of dry tetrahydrofuran, 1.4 g (0.01 mol) of tyramine and 5.0 ml of triethylamine. 3.0 ml of trimethylchlorosilane was then added at ambient temperature, dropwise and with stirring over a period of 30 minutes. Carbon dioxide was thereafter slowly bubbled into the reaction mixture, via a syringe needle for four hours while the mixture was allowed to reflux for the same period. Introduction of carbon dioxide was then terminated, and 1.5 ml of silicon tetrachloride was added slowly using a syringe. After 30 minutes of additional heating, the reaction mixture was allowed to cool, and triethylamine hydrochloride was removed by filtration. The solvent was then removed at 35° C. in vacuo (12 torr), and the resulting oil distilled at 88–90° C. (0.05 torr) to give 2-(4'-trimethylsiloxyphenyl)ethyl isocyanate as a colorless liquid.

The infrared spectrum of this novel compound showed absorption bands at 3.39, 4.41, 6.17 and 6.58μ. The nmr spectrum in CDCl$_3$ showed absorptions at δ7.08 and 6.77 (A$_2$B$_2$q, 4, $J$=8.4 Hz, aromatic 3'-, 5'- and 2'-, 6'-protons, respectively), 3.43 (t, 2, $J$=6.6 Hz, —CH$_2$CH$_2$—N), 2.79 (t, 2,$J$=6.6 Hz, —CH$_2$CH$_2$N) and 0.25 ppm (s, 9, —OSi(CH$_3$)$_3$). The mass spectrum showed a molecular ion at m/e 235, additional peaks at 179, 163, 107 and 73, and a metastable peak at 163.3.

EXAMPLE 2

This Example demonstrates the synthesis of methyl-2-isocyanato-3-(4'-trimethylsiloxyphenyl)propionate (trivially-blocked L-tyrosine methyl ester isocyanate), a compound also capable of being radioiodinated after deblocking. The general procedure described in Example 1 was followed.

Through a stirred mixture of 9.75 g (0.05 mol) of L-tyrosine methyl ester, suspended in 200 ml of dry tetrahydrofuran and 45 ml (0.30 mol) of triethylamine, there was bubbled a stream of dry carbon dioxide. After 30 minutes, 20 ml (0.16 mol) of trimethylchlorosilane was added slowly; and the mixture, with carbon dioxide continuously bubbling through, was allowed to reflux for four hours. The reaction mixture was then allowed to cool to room temperature, the carbon dioxide bubbling discontinued, 8.5 g (6.0 ml, 10.05 mol) of silicon tetrachloride slowly added, and the mixture allowed to stir at ambient temperature for 20 minutes.

The mixture was thereafter allowed to reflux for one hour, then cooled to ambient temperature, and 50 ml of tert-butyl alcohol was added. The mixture was then allowed to stir at ambient temperature for 30 minutes. The mixture was then filtered under nitrogen, the filter cake washed with 30 ml of dry THF, and the combined filtrates concentrated in vacuo and distilled using a short-path column.

The fraction collected at 100°–145° C. (0.05 mm) was redistilled to give 5.8 g (39%) of methyl-2-isocyanato-3-(4'-trimethylsiloxyphenyl)propionate as a viscous, colorless oil: bp 139°–40° C. (0.1 mm); ir (neat smear) 3.38, 4.45 (N=C=O), 5.73 (ester C=O), 6.22, 6.64, 10.9 and 11.8μ; nmr (CCl$_4$) δ7.00 and 6.70 (A$_2$B$_2$q, 4, $J$=8.6 Hz, aromatic 3'-, 5'- and 2'-,6'-protons, respectively), 4.10 (t, 1, $J$=6.0 Hz, —CH$_2$—CH—), 3.66 (s, 3, —OCH$_3$), 2.91 (d, 2, $J$=6.0 Hz, —CH$_2$—CH—) and 0.22 ppm (s, 9, (CH$_3$)$_3$Si—); mass spectrum (70eV) m/e (rel intensity) 293 (5), 278 (1.5), 250 (1), 234 (2.5), 218 (0.75), 179 (100), 163 (2.3), 149 (2), 107 (2), and 73 (40).

EXAMPLE 3

This Example illustrates the synthesis of methyl-2-isocyanato-3-(4'-tert-butyldimethylsiloxyphenyl) propionate; a further compound receptive to radioiodination after deblocking.

The procedure of Examples 1 and 2 was, in general, followed. Into 100 ml of dry tetrahydrofuran, there was added 8.0 g (0.04 mol) of L-tyrosine methyl ester. A slow stream of dry carbon dioxide gas was bubbled into the stirred reaction mixture for 30 minutes while 50 ml of triethylamine was added dropwise. 15 g (0.1 mol) of tert-butyldimethylchlorosilane was then added, and the reaction mixture was heated at reflux for four hours. After cooling, 8.5 g (6.0 ml, 0.05 mol) of silicon tetrachloride was added, whereupon the reaction mixture was stirred for 30 minutes and heated at reflux for one additional hour. 50 ml of tert-butyl alcohol was then added to decompose any silylchlorides and stirring was continued for an additional 30 minutes.

After filtration, washing, and concentration of the reaction mixture as described in the prior Examples, 2.7 g (20 percent yield) of colorless isocyanate boiling at 180° C. (0.5 torr) was isolated. Infrared absorption peaks (smear) were found at 3.38, 4.44, 5.71, 6.17 and 6.53μ. The nmr spectrum (CDCl$_3$) was characterized by signals at δ 7.13 and 6.83 (A$_2$B$_2$q, 4, $J$=8.6 Hz, aromatic 3'-, 5'-, and 2'-, 6'-protons, respectively), 4.26 (t, 1, $J$=6.0 Hz, —CH$_2$CH—), 3.83 (s, 3, —OCH$_3$), 3.08 (d, 2, $J$=6.0 Hz, —CH$_2$CH—), 1.03 (s, 9, —C(CH$_3$)$_3$) and 0.26 ppm (s, 6, —Si(CH$_3$)$_2$). The mass spectrum showed peaks at m/e 335, 278, 250, 236, 221, 205, 172, 73 and 57.

EXAMPLE 4

This Example illustrates the synthesis of 2-trimethylsiloxyethyl isocyanate by the exchange method previously described.

Under nitrogen, 6.1 g (0.1 mol) of ethanolamine and 100 ml of triethylamine dissolved in 100 ml of dry THF was treated with carbon dioxide gas to form the carbamic acid salt. 24 ml (0.2 mol) of trimethylchlorosilane was then added with a syringe and the mixture heated at reflux for two hours. At this point, the carbon dioxide gas treatment was discontinued and the reaction mixture was then cooled, filtered and washed; and the filtrate and washings containing the silylcarbamate were put back into the original flask.

While the mixture was being stirred, 12 ml (0.05 mol) of silicon tetrachloride was added dropwise over a period of fifteeen minutes. The reaction mixture was then allowed to stir overnight, filtered, concentrated under vacuum and distilled to give 2-trimethylsiloxyethyl isocyanate, bp 27°–29° C. at 0.02 millimeters.

The ir (neat smear) showed 3.42, 4.42 (N=C=O), 8.0 (TMS), 9.0, 10.67 and 11.95μ. The nmr spectrum in CDCl₃ showed absorptions at δ3.71 (t, 2, J=5.0 Hz), 3.28 (t, 2, J=5.0 Hz), and 0.16 ppm (s, 9, Si—(CH₃)₃.

EXAMPLE 5

This Example illustrates the synthesis of 3β-O-[O-β-(3β-O-{N-[1-carbomethoxy-2-(4'-hydroxyphenyl)-eth-1-yl]}carbamyldigitoxosyl)-(1→4)-O-β-digitoxosyl-(1→4)-β-digitoxos-1-yl]-12β,14β-dihydroxy-5β-card-20(22)-enolide, trivially-15'-(tyrosine methyl ester)carbamyldigoxin:

tified colorless solid which was not characterized further.

Band three (major), R_f 0.76 (relative mobility=1.17) gave 0.057 g (15%) of 3β-O-[O-β-(3β-O-{N-[1-carbomethoxy-2-(4'-hydroxyphenyl)]-eth-1-yl}carbamyldigitoxosyl)-(1→4)-O-β-digitoxosyl-(1→4)-β-digitoxos-1-yl]-12β, 14β-dihydroxy-5β-card-20(22)-enolide as a glassy, colorless solid: mp 215°-20° C. (dec); uv max (CH₃OH) 222 nm (ε11,930) and 275 nm (ε1,870), ir (KBr), 2.99 (—OH), 3.50, 5.78 (lactone C=O), 5.83

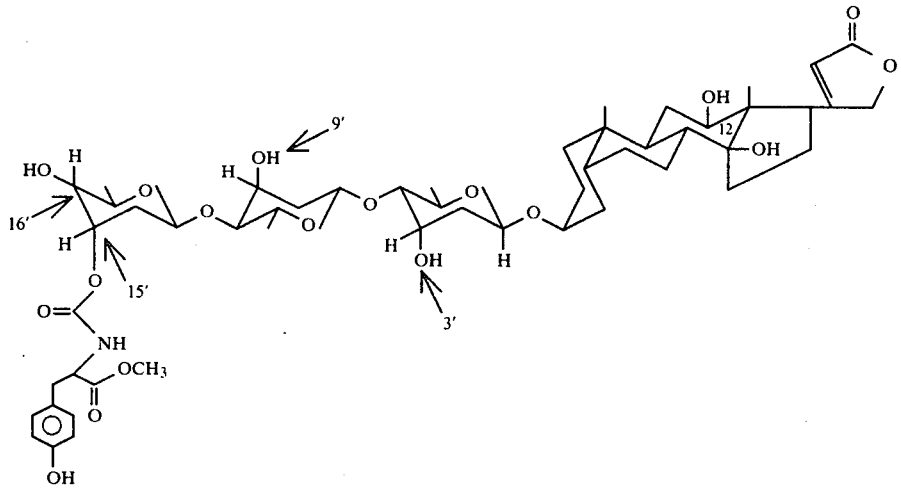

A mixture of 0.300 g (3.84×10⁻⁴ mol) of digoxin (crystalline) and 0.122 g (3.84×10⁻⁴ mol) of methyl-2-isocyanato-3-(4'-trimethylsiloxyphenyl)propionate, made by the method of Example 2, was dissolved in 3 ml of dry pyridine and allowed to stir at 45°-50° C. for six days. The pyridine was then removed in vacuo at ambient temperature, 5 ml of methanol was added and the mixture was allowed to stir for 30 minutes. The volume of methanol was then reduced to about 1 ml in vacuo; and the crude reaction mixture subjected to preparative thin layer chromatography (hereinafter "tlc") on silica gel (20×20×0.2 cm precoated tlc plates) using a 10% methanol-ethyl acetate solvent system.

After development, three major bands and one minor band were observed on the tlc plate under a short wavelength (254 nm) ultraviolet lamp. Visualization of the bands as a series of brownish-black spots was also accomplished by carefully cutting from either vertical edge of the tlc plate a 1.5×20 cm strip using a glass cutter, spraying the strip lightly with an aerosol of concentrated sulfuric acid and heating at 100° C. until the spots become well defined. A direct comparison of this strip with the remainder of the tlc plate was then used as an alternate means of band location. All bands were scraped from the plate and eluted with 10% methanol-methylene chloride and the solvent removed in vacuo at ambient temperature.

The first major band, R_f 0.65 (for more accurate comparison to the other three components, relative mobility is assigned 1.0) contained 0.120 g (40%) of a white solid, mp 241°-4° C. This material was identified as digoxin by comparison with an authentic sample.

The second band (minor), R_f 0.7 (relative mobility= 1.07) contained trace amounts (<0.001 g) of an unidentified (ester C=O), 6.19, 6.65, 6.95, 7.27, 7.35, 7.96, 8.20, 8.63, 9.22, 9.41, 9.86, 11.56, 12.01, 12.23 and 12.54μ; nmr (50% CDCl₃-acetone-d₆)δ7.73 (s, 1, aromatic-OH), 6.97 and 6.70 (A₂B₂q, 4, J=8.6 Hz, tyrosine 3'-, 5'- and 2'-, 6'-protons, respectively), 5.91 (s, 1, lactone-C=CH—), 3.74 (s, 3, ester-OCH₃), 0.93 (s, 3, 19-CH₃), and 0.83 ppm (s, 3, 18-CH₃), trivially: 15'-(TME)carbamyldigoxin.

The fourth band (major) R_f 0.79 (relative mobility=1.22) contained 0.067 g (16%) of 3β-O-[O-β-(3β-O-{N-[1-carbomethoxy-2-(4'-hydroxyphenyl)-eth-1-yl]}carbamyldigitoxosyl)- (1→4)-O-β-digitoxosyl-(1→4)-β-digitoxos-1-yl]-12β-O-{N-[1-carbomethoxy-2-(4'-hydroxyphenyl)-eth-1-yl]carbamyl}-14β-hydroxy-5β-card-20(22)-enolide as a glassy, colorless solid: mp 220°-4° C. (dec); uv max (CH₃OH) 222 nm (ε22,050) and 273 nm (ε11,540); ir (KBr) 3.01 (OH), 3.47, 5.78 (lactone C=O)) 5.82 (ester C=O), 6.17, 6.63, 6.95, 7.28, 7.35, 7.95, 8.19, 8.58, 8.87, 9.17. 9.40, 9.86, 10.05, 11.52, 11.89, 12.12 and 12.45μ; nmr (60 MHz, 50% CDCl₃-acetone-d₆)δ7.61 (s, 1, aromatic-OH), 7.06 and 6.78 (A₂B₂ q, 4, J=8.6 Hz, tyrosine 3'-, 5'- and 2'-, 6'-protons, respectively) 7.02 and 6.78 (A₂B₂q, 4, J=8.6 Hz, tyrosine 3'-5'- and 2'-, 6'-protons, respectively), 5.91 (s, 1, lactone-C=CH-), 3.75 (s, 6, ester-OCH₃), 0.93 (s, 3, 19-CH₃) and 0.83 ppm (s, 3, 18-CH₃); nmr (220 MHz, DMSO-d₆) δ7.37 (s, 1, aromatic OH), 7.03 and 6.99 (A₂B₂q, 4, J=8.0 Hz, tyrosine 3'-, 5'- and 2'-, 6'-protons, respectively), 6.66 and 6.64 (A₂B₂q, 4, J=8.0 Hz, tyrosine 3'-, 5'- and 2'-, 6'-protons, respectively), 5.90 (s, 1, lactone-CH=CH-), 3.61 (s, 3, ester OCH₃), 3.60 (s, 1, ester OCH₃), 0.84 (s, 3, 19-CH₃) and 0.76 ppm (s, 3, 18-CH₃), trivially: 12,15'-(diTME)carbamyldigoxin.

EXAMPLE 6

To a mixture of 2.0 millicuries of sodium iodide-$^{125}$I solution, 25 μl of 0.5 M potassium phosphate buffer, pH 7.5, and 2 μg of 15'-(TME)carbamyldigoxin dissolved in 20 μl of methanol in a disposable 1.5 ml micro-sample tube was added at once 50 μg of chloramine T (N-chloro-p-toluenesulfonamide, sodium salt trihydrate) dissolved in 20 μl of 0.05 M potassium phosphate buffer, pH 7.5. After exactly 20 seconds, 100 μg of sodium metabisulfite dissolved in 20 μl of 0.05 M potassium phosphate buffer, pH 7.5, was added to terminate the reaction.

A 1 μl sample of the reaction mixture was applied to an analytical silica gel tlc plate (5×20×0.025 cm), and the remainder was applied in a 6×0.2 cm band to a preparative-layer silica gel tlc plate (20×20×0.2 cm) at a line 2 cm from the bottom edge of the plate. The plates were allowed to air dry for 15 minutes and then developed using a 10% methanol-chloroform solvent system until the solvent front reached the top of each plate. The plates were allowed to air dry for 30 minutes then wrapped with thin, transparent polyethylene film and analyzed with x-ray film and a radiochromatogram scanner to locate and quantitate radioactive bands on the plates.

Each plate typically showed three radioactive bands (spots on the analytical tlc plate). The band at the origin, $R_f$ 0.0, typically contained 200 μCi (10% of total radioactivity) and corresponded to unreacted $^{125}$I.

The major band $R_f$ 0.28 (preparative tlc) and 0.35 (analytical tlc) contained 1600 μCi (80% of total radioactivity of 3β-O-[O-β-{3β-O-[N-{1-carbomethoxy-2-[4'-hydroxy-3'-($^{125}$I)-iodophenyl]}-eth-1-yl]carbamyldigitoxosyl}-(1→4)-O-β-digitoxosyl-(1→4)-β-digitoxos-1-yl]-12β,14β-dihydroxy-5β-card-20(22)-enolide (trivial name: 15'-(TME)carbamyldigoxin-$^{125}$I). This band was scraped off the preparative tlc plate, transferred to a 15×0.9 cm glass column fitted with a glass wool plug at the bottom, and eluted in 1 ml aliquots with 30 ml of a 10% methanol-chloroform solvent system. The combined eluate was evaporated to dryness with a stream of dry nitrogen, the residue dissolved in 0.5 ml of absolute ethanol, applied to a (20×20×0.025 cm) analytical tlc plate and allowed to develop using a 10% methanol-chloroform solvent system. The tlc plate was then air dried, wrapped with thin, transparent polyethylene film and analyzed by autoradiography using x-ray film to locate radioactive bands on the plate. The radioactive band corresponding to 15'-(TME)carbamyldigoxin-$^{125}$I was scraped off the tlc plate, transferred to a 15×0.9 cm glass column fitted with a glass wool plug at the bottom, and eluted from the silica gel with 30 ml of a 10% methanol-chloroform solution applied to the column in 3 ml portions. The total eluate was evaporated with a stream of dry nitrogen and the residue dissolved in 1 ml of absolute ethanol. Thin layer chromatography on silica gel (5×20×0.025 cm) showed the presence of one homogeneous spot using a 10% methanol-chloroform solvent system. The purified material, stored at −20° C., was stable for several months.

The third band (minor), $R_f$ 0.34 (preparative tlc) and 0.43 (analytical tlc) contained 300 μCi (15% of total radioactivity of 3β-O-[O-β{3β-O-[N-{1-carbomethoxy-2-[4'-hydroxy-3', 5'-($^{125}$I)-diiodophenyl]}-eth-1-yl]carbamyldigitoxosyl}- (1→4)-O-β-digitoxosyl-(1→4)-β-digitoxos-1-yl]-12β, 14β-dihydroxy-5β-card-20(22)-enolide (trivial name 15'-(TME)carbamyldigoxin-di-$^{125}$I). This band was scraped off the preparative tlc plate, transferred to a 15×0.9 cm glass column fitted with a glass wool plug at the bottom, and eluted with 30 ml of a 10% methanol-chloroform solvent system. The combined eluate was evaporated to dryness with a stream of dry nitrogen, the residue dissolved in 0.5 ml of absolute alcohol and stored at −20° C.

EXAMPLE 7

This Example demonstrates the synthesis of 17β-O-{N-[2-(4'-hydroxyphenyl)-ethyl]}carbamylandrost-4-ene-3-one, trivially-17-(tyramine) caramyltestosterone:

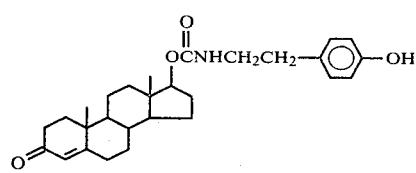

This was prepared in the same manner as described in Example 5 by reacting 0.25 g of testosterone with 0.24 g of 2-(4'-trimethylsiloxyphenyl)ethyl isocyanate (made in Example 1) in 5 ml of methylene chloride at 50° C. for three days. The crude product was obtained by evaporation of the solvent. Removal of the blocking group with methanol followed by crystallization from the same solvent gave 0.100 g of the subject compound, mp 244°–6° C. Tlc on silica gel (20×5×0.025 cm plate) using a 5% methanol-chloroform solvent system showed an $R_f$ of 0.46 for this compound.

This compound was characterized by infrared spectroscopy (KBr) and gave absorptions at 3.05 (OH), 3.40, 5.92 (carbamate carbonyl), 6.02 (vinyl carbonyl), 6.20 (aromatic), 6.60, 6.90, 7.90, 8.10, 9.52, 9.90, 11.60 and 11.98μ.

The nmr spectrum in 30% CF$_3$CO$_2$H-CDCl$_3$ displayed signals at δ7.26 (s, 1, aromatic O$\underline{H}$), 7.08 and 6.82 (A$_2$B$_2$q, 4, $\underline{J}$=8.4 Hz, tyramine 3'-,5'-and 2'-,6'-protons, respectively), 5.96 (s, 1,—C$\underline{H}$=C—), 1.25 (s, 3, 19-C$\underline{H}_3$) and 0.86 ppm (s, 3, 18-C$\underline{H}_3$).

Elemental analysis: calculated C 74.46%, H 8.25%, N 3.1%; found C 74.35%, H 8.05%, and N 3.3%.

EXAMPLE 8

This Example illustrates the synthesis of 21-O-{N-[2-(4'-hydroxyphenyl)-ethyl]}carbamylpregn-4-ene-11β, 17α-diol-3,20-dione, trivially-21-(tyramine) carbamylcortisol:

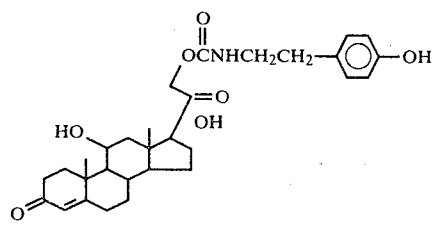

0.150 g of cortisol was allowed to react with 0.240 g of 2-(4'-trimethylsiloxyphenyl)ethyl isocyanate in 2 ml of pyridine at ambient temperature for four hours. After evaporation of the solvent in vacuo and cleavage of the blocking group by methanol, the carbamate was isolated by preparative tlc on silica gel using a 20% methanol-chloroform solvent system ($R_f$ 0.63).

The infrared spectrum of this compound (KBr) was characterized by the following bands: 2.98 (hydroxyl), 3,42, 5.80 (carbamate C=O), 5,85 (C20 C=O), 6.04 (vinyl C=O), 6.62, 6.88, 7.05, 7.20, 7.35, 7.90, 8.10, 8.52, 8.80, 8.95, 9.45, 9.70, 11.55, 12.05, 12.80 and 14.70μ.

The nmr spectrum in 50% CDCl$_3$-DMSO-d$_6$ showed signals at δ 7.55 (s, 1, aromatic O$\underline{H}$), 7.02 and 6.73 (A$_2$B$_2$q, 4, $\underline{J}$=8.2 Hz, tyramine 3'-,5'-and 2'-,6'-protons, respectively), 5.63 (s, 1, —C$\underline{H}$=C), 1.44 (s, 3, 19-C$\underline{H}_3$) and 0.89 ppm (s, 3, 18-C$\underline{H}_3$).

EXAMPLE 9

This Example shows the preparation of 3-O{N-[2-(4'-hydroxyphenyl)-ethyl]}carbamylestra-1,3,5(10)-triene-17-one, trivially-3-(tyramine)carbamylestrone:

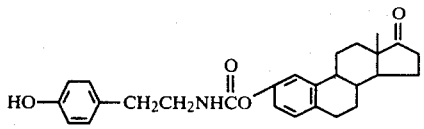

In the same general manner as described in Example 5, this was synthesized from 0.190 g of estrone and 0.360 g of 2-(4'-trimethylsiloxyphenyl)ethyl isocyanate dissolved in a mixture of 3 ml of triethylamine, 0.5 ml of dioxane and 0.050 g of triphenylphosphine as catalyst, and held at 70° C. for 24 hours. After evaporation of the solvents in vacuo, followed by removal of the blocking group with methanol, the subject compound was isolated by preparative tlc on silica gel (20×20×0.2 cm plate) using a 2% methanol-chloroform solvent system (R$_f$0.48).

The infrared spectrum (smear) showed bands at 3.03 (hydroxyl), 3.43, 5.82 (broad carbonyl), 6.22, 6.68, 6.93, 7.40, 8.20, 9.50, 12.20 and 13.30μ.

The nmr spectrum (CDCl$_3$) showed signals at δ7.15 (m, 8 aromatic protons and aromatic O$\underline{H}$) and 0.83 ppm (s, 3, 18-C$\underline{H}_3$).

EXAMPLE 10

This Example shows the preparation of 3β-O-[O-β-(3β-O-{N-[2-(4'-hydroxyphenyl)eth-1-yl]}carbamyl-digitoxosyl)-(1→4)-O-β-digitoxosyl-(1→4)-β-digitoxos-1-yl]-12β, 14β-dihydroxy-5β-card-20(22)-enolide, trivially-15'-(ryramine) carbamyldigoxin:

A mixture of 0.200 g (2.56 ×10$^{-4}$ mol) of digoxin (crystalline) and 0.061 g (2.56 ×10$^{-4}$ mol) of 2-(4'-trimethylsiloxyphenyl)ethyl isocyanate, made by the method of Example 1 was dissolved in 3 ml of dry pyridine and allowed to stir at 45°-50° C. for seven days. The pyridine was then removed in vacuo at ambient temperature, 5 ml of methanol was added and the mixture was allowed to stir for 30 minutes. The volume of methanol was then reduced to about 1 ml in vacuo and the crude reaction mixture subjected to preparative thin layer chromatography on silica gel using a 10% methanol-ethyl acetate solvent system. After development, two major bands, in addition to one for unreacted digoxin, were observed on the tlc plate under 254 nm (ultraviolet) light.

The first band, R$_f$0.44 contained 0.03 g of 15'-(tyramine) carbamyldigoxin. This derivative, characterized by infrared spectroscopy (KBr) gave the following bands: 2.95 (hydroxyl), 3.45, 5.80 (broad carbonyl), 6.18, 6.63, 6.90, 7.28, 8.55, 8.85, 9.35, 11.50, 12.10, and 13.75μ. The nmr spectrum in 50% CDCl$_3$-acetone-d$_6$ showed signals at δ7.55 (s, 1, aromatic O$\underline{H}$), 7.05 and 6.79 (A$_2$B$_2$q, 4, $\underline{J}$=8.4 Hz, tyramine 3'-,5'-' and 2'-,6'-protons, respectively), 5.90 (s, 1, lactone C=C$\underline{H}$—), 0.93 (s, 3, 19-C$\underline{H}_3$) and 0.83 ppm (s, 3, 18-C$\underline{H}_3$).

The second major band, R$_f$ 0.55 gave 0.030 g of 12,15'-(dityramine)-carbamyldigoxin and was characterized in its nmr spectrum (50% CDCl$_3$-acetone-d$_6$) by bands at δ7.73 (s, 1, aromatic O$\underline{H}$), 7.08 and 6.76 (A$_4$B$_4$q, 8, $\underline{J}$=8.6 Hz, tyramine 3'-,5'-and 2'-, 6'-protons, respectively), 5.86 (d, 1, lactone C=C$\underline{H}$), 0.93 (s, 3, 19-C$\underline{H}_3$) and 0.83 ppm (s, 3, 18-C$\underline{H}_3$).

EXAMPLE 11

This Example demonstrates the preparation of 15'-(tyramine)carbamyldigoxin using a photoassisted reaction as described in Bruner et al., Journal of the Chemical Society, Chemical Communications, page 253 (1974).

To 0.100 g (1.28×10$^{-4}$ mol) of digoxin suspended in 100 ml of degassed carbon tetrachloride was added 0.032 g (1.36×10−4 mol) of 2-(4'-trimethylsiloxyphenyl)ethyl isocyanate and 0.003 g (1.61×10−5 mol) of ferrocene. The reaction mixture was allowed to stir at ambient temperature for 12 hours under constant exposure to light from a tungsten lamp. The solvent was

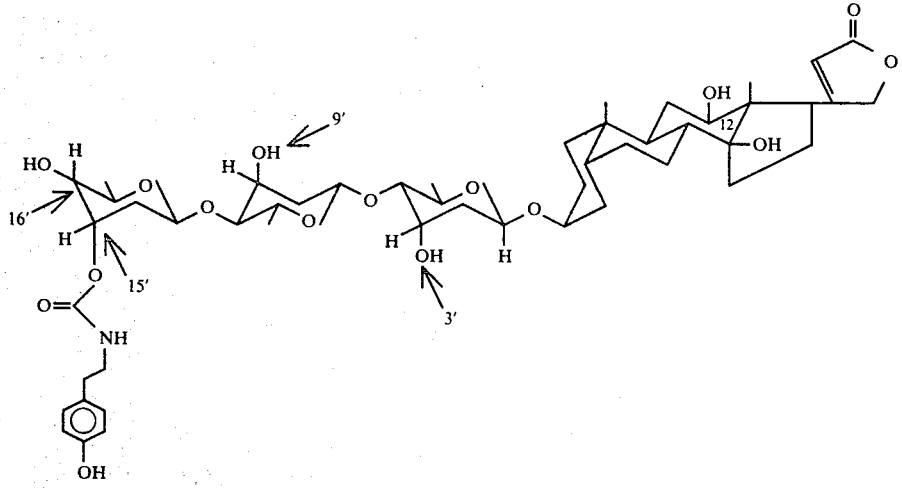

removed under reduced pressure and the resulting residue dissolved in methanol to remove the trimethylsilyl blocking group.

Purification of the crude product by preparative tlc as described in Example 10 gave 0.025 g of 15'-(tyramine)- carbamyldigoxin. No 12,15'-(dityramine)-carbamyldigoxin was detected.

EXAMPLE 12

This Example shows the synthesis of 3β-O-{N-[2-(4'-hydroxyphenyl)-ethyl]}carbamyl-12β, 14β-dihydroxy-5β-card-20(22)-enolide, trivially-3-(tyramine)carbamyldigoxigenin:

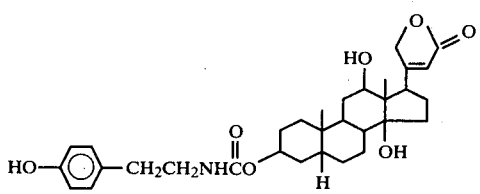

Using the same general procedure as described in Example 5, 0.100 g of digoxigenin was allowed to react with 0.220 g of 2-(4'-trimethylsiloxyphenyl)-ethyl isocyanate in 2 ml of dry pyridine at 80° C. for 24 hours. The solvent was then removed in vacuo and the residue treated with methanol to remove the trimethylsilyl blocking group. Purification of the crude compound by preparative tlc on silica gel using a 10% methanol-ethyl acetate solvent system gave 0.025 g of the subject compound ($R_f$ 0.57).

The infrared spectrum of this compound (KBr) showed absorptions at 3.00 (hydroxyl), 3.48, 5.85 (broad carbonyl), 6.20, 6.62, 6.92, 7.05, 7.40, 7.95, 8.20, 8.55, 9.05. 9.72, 10.10, 10.50 and 12.00μ.

The nmr spectrum in methanol-$d_4$ showed signals at δ7.88 (s, 1, aromatic O$\underline{H}$), 7.05 and 6.70, (A$_2$B$_2$q, 4, $\underline{J}$=8.2 Hz, tyramine 3'-,5'-and 2'-,6'-protons, respectively), 5.83 (s, 1, lactone C=C$\underline{H}$), 0.96 (s, 3, 19-C$\underline{H}_3$) and 0.85 ppm (s, 3, 18-C$\underline{H}_3$).

EXAMPLE 13

This Example illustrates the synthesis of 21-O-{N-[1-carbomethoxy-2-(4'-hydroxyphenyl)ethyl]}carbamyl-pregn-4-ene-11β,17α-diol-3,20-dione, trivially-21-(tyrosine methyl ester)carbamylcortisol:

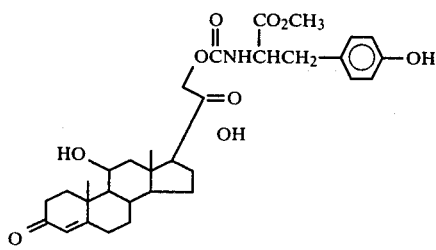

Using the same general procedure as described in Example 5, 0.362 g of cortisol was allowed to react with 0.297 g of methyl-2-isocyanato-3-(4'-trimethylsiloxyphenyl) propionate in 5 ml of dry pyridine at ambient temperature for four days. After removal of the solvent in vacuo, the crude reaction mixture was dissolved in methanol to remove the blocking group and purified by preparative thin layer chromatography on silica gel using a 50% chloroform-acetone solvent system to give 0.445 g of the subject compound ($R_f$ 0.64).

Characterization by infrared spectroscopy (KBr) gave bands at 3.00 (hydroxyl), 3.48, 5.82, (broad carbonyl), 6.05, (vinyl carbonyl), 6.65, 6.98, 7.35, 7.90, 8.20, 9.05, 9.48, 10.60, 10.93, 11.10, 11.55, 11.85, 12.00, 12.48, 12.80 and 13.65μ.

The nmr spectrum in 50% CDCl$_3$-acetone-$d_6$ displayed signals at δ7.66 (s, 1, aromatic O$\underline{H}$), 7.05 and 6.75 (A$_2$B$_2$q, 4, $\underline{J}$=8.4 Hz, tyrosine 3'-,5'-and 2'-,6'-protons, respectively), 5.65 (s, 1, C=C$\underline{H}$), 3.75 (s, 3, —OC$\underline{H}_3$), 1.46 (s, 3, 19-C$\underline{H}_3$) and 0.93 ppm (s, 3, 18-C$\underline{H}_3$).

EXAMPLE 14

This Example demonstrates the synthesis of 17β-O-{N-[1-carbomethoxy-2-(4'-hydroxyphenyl)ethyl]}carbamylandrost-4-ene-3-one, trivially-17-(tyrosine methyl ester) carbamyltestosterone:

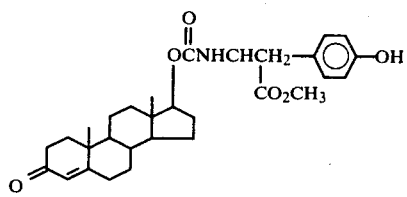

In the same manner as described in Example 5, 0.200 g of testosterone was allowed to react with 0.280 g of methyl-2-isocyanato-3-(4'-trimethylsiloxyphenyl)propionate in 3 ml of dry pyridine at 50° C. for four days. The solvent was then removed under reduced pressure and the resulting residue treated with methanol to remove the trimethylsilyl blocking group. Purification by preparative tlc on silica gel using a 10% methanol-ethyl acetate solvent system gave 0.063 g of the subject compound ($R_f$ 0.68).

The infrared spectrum (KBr) showed absorptions at 2.99 (hydroxyl), 3.40, 5.85 (broad carbonyl), 6.19 (vinyl carbonyl), 6.68, 6.95, 7.42, 7.90, 8.30, 9.45, 11.55, 12.10, 12.50 and 12.90μ.

The nmr spectrum (CDCl$_3$) showed signals at δ7.26 (s, 1, aromatic O$\underline{H}$), 6.98 and 6.73 (A$_2$B$_2$q, 4, $\underline{J}$=8.6 Hz, tyrosine 3'-,5'-and 2'-,6'-protons, respectively), 5.73 (s, 1, C=C$\underline{H}$), 3.73 (s, 3, OC$\underline{H}_3$), 1.16 (s, 3, 19C$\underline{H}_3$) and 0.76 ppm (s, 3, 18-C$\underline{H}_3$).

EXAMPLE 15

This Example shows the synthesis of 3β-O-{N-[1-carbomethoxy-2-(4'-hydroxyphenyl)ethyl]}carbamyl-12β, 14β-dihydroxy-5β-card-20(22)-enolide, trivially-3-(tyrosine methyl ester)carbamyldigoxigenin:

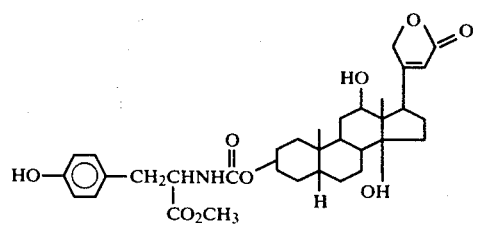

Using the general procedure as described in Example 5, a mixture of 0.100 g of digoxigenin and 0.085 g of methyl-2-isocyanato-3-(4'-trimethylsiloxyphenyl)propionate in 1.5 ml of dry pyridine was allowed to stir at 70° C. for three days. The solvent was then removed in vacuo, the crude product dissolved in methanol to remove the trimethylsilyl blocking group and then subjected to preparative tlc on silica gel using a 5% methanol-ethyl acetate solvent system. A yield of 0.029 g of the subject compound was obtained ($R_f$ 0.60).

Infrared spectroscopy on this compound indicated bands at 3.00 (hydroxyl), 3.45, 5.80 (broad carbonyl), 6.20, 6.65, 7.00, 7.38, 7.95, 8.20, 9.55, 9.80 and 12.00μ.

The nmr spectrum in 50% CDCl₃-acetone-d₆ displayed bands, at δb 7.51 (s, 1, aromatic OH), 7.03 and 6.79 (A₂B₂q, 4, J=8.6 Hz, tyrosine 3'-,5'- and 2'-,6'-protons, respectively), 5.93 (s, 1, lactone C=CH), 3.75 (s, 3, OCH₃), (s, 3, 19CH₃) and 0.86 ppm (s, 3, 18-CH₃).

EXAMPLE 16

This example shows the synthesis of 3β-O-[O-β-(3β-O-{N-[1-carbomethoxy-2-(4'-hydroxyphenyl)]-eth-1-yl}carbamyldigitoxosyl)-(1→4)-O-β-digitoxosyl-(1→4)-β-digitoxos-1-yl]-14β-hydroxy-5 $\mathit{6}2$ -card-20(22)-enolide, trivially-15'-(tyrosine methyl ester)carbamlydigitoxin:

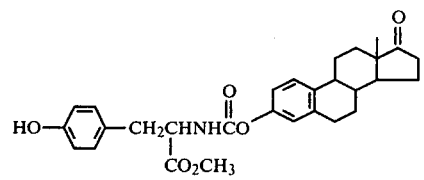

In the same general manner as described in Example 5, a mixture of 0.200 g of estrone and 0.250 g of methyl-2-isocyanato-3-(4'-trimethylsiloxyphenyl)propionate in 3 ml of dry pyridine was allowed to react at 60° C. for five days. After removal of the solvent in vacuo, the crude reaction mixture was dissolved in methanol to remove the blocking group. Purification by preparative tlc on silica gel using a 5% methanol-chloroform solvent system gave 0.079 g of the subject compound ($R_f$ 0.68).

The infrared spectrum of this compound showed bands at 3.00 (hydroxyl), 3.42, 5.78 (broad carbonyl), 6.23, 6.65, 6.95, 7.35, 7.95, 8.22, 8.50, 9.53, 10.00, 10.95,

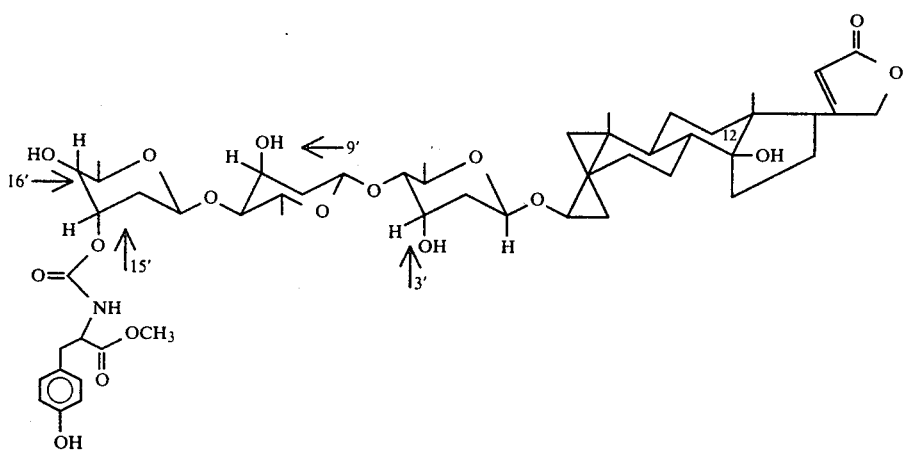

Following the general procedure of Example 5, a mixture of 0.200 g of digitoxin and 0.100 g of methyl2-isocyanato-3-(4'-trimethylsiloxyphenyl)propionate in 2.5 ml of dry pyridine was allowed to react at 50° C. for five days. The solvent was then removed under reduced pressure and the crude reaction mixture treated with methanol to remove the blocking group. Purification of the crude product by preparative tlc on silica gel using a 10% methanol-ethyl acetate solvent system gave 0.134 g of the subject compound ($R_f$ 0.71).

The infrared spectrum showed bands at 2.95 (hydroxyl), 3.42, 5.85 (broad carbonyl), 6.20, 6.65, 6.95, 7.35, 7.95, 8.28, 8.65, 8.90, 9.40 (broad), 11.60 and 12.20μ.

The nmr spectrum (50% CDCl₃-acetone-d₆) showed signals at δ7.71 (s, 1, aromatic OH), 6.93 and 6.63 (A₂B₂q, 4, J=8.6 Hz, tyrosine 3'-,5'- and 2'-,6'-protons, respectively), 5.78 (s, 1, lactone C=CH), 3.61 (s, 3, OCH₃), 0.83 (s, 3, 19-CH₃) and 0.73 ppm (s, 3, 18-CH₃).

EXAMPLE 17

This Example illustrates the synthesis of 3-O-{N-[1-carbomethoxy-2-(4'-hydroxyphenyl)ethyl]}carbamylestra-1,3,5(10)-triene-17-one, trivially-3-(tyrosine methyl ester) carbamylestrone:

12.00 and 12.90μ.

The nmr spectrum in CDCl₃ showed signals at δ 6.83 (m, 7, aromatic protons), 3.66 (s, 3, OCH₃), and 0.81 ppm (s, 3, 18-CH₃).

EXAMPLE 18

This Example demonstrates the synthesis of 3-O-{N-[1-carbomethoxy-2-(4'-hydroxyphenyl)]=carbamyl-17β-hydroxyestra-1,3,5(10)-triene, trivially-3-(tyrosine methyl ester) carbamylestradiol:

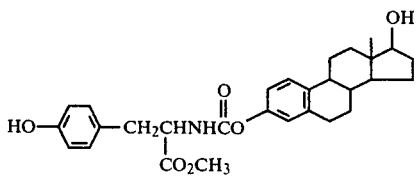

The reactive 17β-hydroxyl group was first blocked with a trimethylsilyl (TMS) group. A mixture of 0.272 g of 17β-estradiol and 2 ml (excess) of trimethylsilyl-N, N-dimethyl carbamate was allowed to stir at ambient temperature for one hour to block both hydroxyls with TMS groups. Unreacted trimethylsilyl-N, N-dimethyl carbamate was then removed under reduced pressure at ambient temperature.

To selectively remove the 3-TMS groups while leaving the 17-TMS group intact, the crude reaction mixture was then dissolved in 40 ml of a 50% methanol-chloroform solution; and the solution was allowed to reflux for two hours. The selective deblocking of the 3-hydroxyl group was monitored by nmr spectroscopy as follows. In the 3,17-di(TMS)-substituted derivature (CDCl$_3$ solvent) two sharp singlets of equal intensity, corresponding to the 3- and 17-TMS groups appeared 30 and 38.6 Hz upfield, respectively, of the 18-methyl group signal. As the deblocking proceeded, the signal at 30 Hz upfield (3-TMS) disappeared while the signal at 38.6 Hz upfield remained unchanged. The solvent was then removed in vacuo at ambient temperature to give 0.345 g of the 3-hydroxy-,17-TMS-blocked compound.

This entire quantity of intermediate was then allowed to react with 0.400 g of methyl-2-isocyanato-3-(4'-tert-butyldimethylsiloxyphenyl)propionate in 4 ml of dry pyridine for five days at ambient temperature. The solvent was then removed under reduced pressure and the resulting crude product purified by preparative tlc on silica gel using a 10% methanol-chloroform solvent system to give 3-O-{N-[1-carbomethoxy-2-(4'-tert-butyldimethylsiloxyphenyl) ethyl]}carbamyl-17β-trimethylsiloxyestra-1,3,5(10)-triene as a pure compound, R$_f$ 0.6.

To remove both of the silyl blocking groups, a mixture of 0.080 g of this compound dissolved in 5 ml of dioxane, 1 ml of methanol and 0.200 g of tetraethylammonium fluoride dissolved in 1 ml of distilled water was allowed to stir at ambient temperature for two days. The solvents were then removed in vacuo at ambient temperature, the resulting solid was washed with distilled water and dried under reduced pressure to give the pure subject compound.

The infrared spectrum (smear) of the pure compound displayed bands at 3.00 (hydroxyl), 3.42, 5.90 (broad carbonyl), 6.23, 6.68, 6.95, 7.42, 8.22, 9.45, 11.50, 12.20 and 12.90μ.

The nmr spectrum (acetone-d$_6$) showed signals at δ 6.85 (m, 7, aromatic protons), 3.66 (s, 3, OCH$_3$) and 0.76 ppm (s, 3, 18-CH$_3$).

EXAMPLE 19

This Example shows the synthesis of 3-O-{N-[1-carbomethoxy-2-(4'-hydroxyphenyl)]}carbamyl-16α,17β-dihydroxyestra-1,3,5(10)-triene, trivially-3-(tyrosine methyl ester) carbamylestriol:

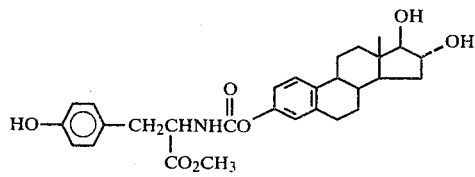

The reactive 16α- and 17β-hydroxyl groups were first blocked with trimethylsilyl (TMS) groups. To this end, a mixture of 0.228 g of estriol and 2 ml (excess) of trimethylsilyl-N,N-dimethyl carbamate was allowed to stir at 50° C. for two hours to block all three hydroxyls with TMS groups. Unreacted trimethylsilyl-N,N-dimethyl carbamate was then removed under reduced pressure at ambient temperature.

To selectively remove the 3-TMS group while leaving the 16- and 17-TMS groups intact, the crude reaction mixture was then dissolved in 40 ml of a 50% methanol-chloroform solution; and the solution was allowed to reflux for four hours. The selective deblocking of the 3-hydroxyl group was monitored by nmr spectroscopy as follows. In the 3,16,17-tri(TMS)-substituted derivature (CDCl$_3$) two sharp singlets of relative intensity 1:2, corresponding to the 3- and coincident 16-, 17-TMS groups appeared 30.6 and 36.6 Hz upfield, respectively, of the 18-methyl group signal. As the blocking proceeded, the signal at 30.6 Hz upfield (3-TMS) disappeared while the signal at 36.6 Hz upfield remained unchanged. The solvent was then removed in vacuo at ambient temperature to give 0.434 g (1.0×10$^{-3}$ mol) of the 3-hydroxy-, 16,17-di(TMS)-blocked compound.

The entire 0.434 g of this intermediate was then allowed to react with 1.47 g (5.0×10$^{-3}$ mol) of methyl-2-isocyanato-3-(4'-tert-butyldimethylsiloxyphenyl)-propionate in 3ml of dry pyridine for three days at 64° C. The solvent was then removed under reduced pressure, and the resulting crude product purified by preparative tlc on silica gel using a 10% methanol-methylene chloride solvent system to give 0.060 g of 3-O-{N-[1-carbomethoxy-2-(4'-tert-butyldimethylsiloxyphenyl)ethyl]}carbamyl-16α,17β-bis-trimethylsiloxyestra-1,3,5(10)-triene as a pure compound, R$_f$ 0.5.

To remove both of the silyl blocking groups, a mixture of 0.060 g of this compound dissolved in 10 ml of dioxane and 0.150 g of tetraethylammonium fluoride dissolved in 0.5 ml of distilled water was allowed to stir at ambient temperature for one day. The solvents were then removed in vacuo at ambient temperature, the resulting solid was washed with distilled water and dried under reduced pressure to give the pure subject compound.

The infrared spectrum of this compound (smear) displayed bands at 3.00 (hydroxyl), 3.44, 5.90 (broad carbonyl), 6.22, 6.68, 6.95, 7.37, 8.15, 8.52, 9.45, 10.95, 12.15 and 12.75μ.

The nmr spectrum (acetone-d$_6$) showed signals at δ 8.00 (s, 1, aromatic OH), 6.84 (m, 7, aromatic protons), 3.70 (s, 3, OCH$_3$) and 0.81 ppm (s, 3, 18-CH$_3$).

EXAMPLE 20

This Example demonstrates the synthesis of 11α-O-{N-[1-carbomethoxy-2-(4'-hydroxyphenyl)ethyl]}carbamylpregn-4-ene-3,20-dione, trivially-11-(tyrosine methyl ester) carbamylprogesterone:

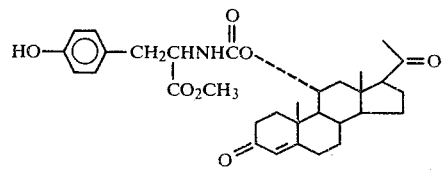

Using the same general procedure as described in Example 5, 0.166 g (5×10$^{-4}$ mol) of 11α-hydroxyprogesterone was allowed to react with 0.002 g (6×10$^{-4}$ mol) of methyl-2-isocyanato-3-(4'-trimethylsiloxyphenyl)propionate in 4 ml of dry pyridine at 60° C. for three days. The solvent was removed in vacuo, and the crude reaction mixture was dissolved in methanol to remove the trimethylsilyl group. Purification by preparative thin layer chromatography on silica gel using a 10% methanol-ethyl acetate solvent system gave 0.207 g of the subject compound ($R_f$ 0.71).

The infrared spectrum (KBr) showed bands at 3.10 (hydroxyl), 3.50, 5,80 (broad carbonyl), 6.00, 6.65, 6.98, 7.45, 8.25, 9.55 and 12.00μ.

The nmr spectrum (CDCl$_3$) displayed signals at δ 6.98 (m, 5, aromatic protons and OH); 5.76 (s, 1, CH=C), 3.78 (s, 3, OCH$_3$), 2.11 (s, 3, CH$_3$C=O), 1.23 (s, 3, 19-CH$_3$) and 0.70 ppm (s, 3, 18-CH$_3$).

EXAMPLE 21

This Example demonstrates the synthesis of, trivially, 6-(TME)ureidonicotine, a nicotine analog-isocyanate adduct suitable for carrying out a nicotine assay:

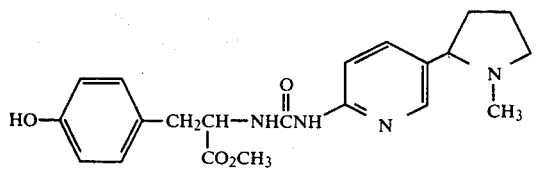

A mixture of 0.280 g (0.00158 mol) of 6-aminonicotine and 0.500 g (0.0017 mol) of methyl-2-isocyanato-3-(4'-trimethylsiloxyphenyl) propionate (made by the method of Example 2) was dissolved in 5 ml of dry pyridine and allowed to stir at ambient temperature overnight. The pyridine was then removed in vacuo at ambient temperature and 5 ml of methanol was added, and the mixture was allowed to stir for an additional 30 minutes.

The reaction mixture was then concentrated to about 1 ml in vacuo and subjected to preparative thin layer chromatography on silica gel (20×20×0.2 cm plate) using a 20% methanol-ethyl acetate solvent system to give the subject urea, $R_f$ 0.23.

This compound was characterized by infrared spectroscopy (KBr) and gave absorptions at 3.1, 3.2 (NH), 5.8 (ester carbonyl), 5.98 (urea carbonyl), 6.2, 6.3, 6.5, 6.7, 8.2 and 12.00μ. The ultraviolet absorption spectrum in 0.1 N NaOH displayed maxima at 286 nm (ε9540) and 237 nm (ε35,100). The nmr spectrum in DMSO-d$_6$ was characterized by bands at δ9.36 (s, 1, NH), 8.80 (broad d, 1, NHCH), 8.41 (s, 1, OH), 7.77 (m, 2, 2- and 4-protons), 6.98 and 6.66 (A$_2$B$_2$q, 4, $J$=9.0 Hz, tyrosine 3'-, 5'- and 2'-,6'-protons), 4.50 (s, 1, tyrosine CHCH$_2$), 3.61 (s, 3, CO$_2$CH$_3$) and 2.09 ppm (s, 3, NCH$_3$).

EXAMPLE 22

This Example illustrates the preparation of a further nicotine analog-isocyanate adduct useful in carrying out a nicotine assay, the compound trivially being 2-(TME)ureidonicotin

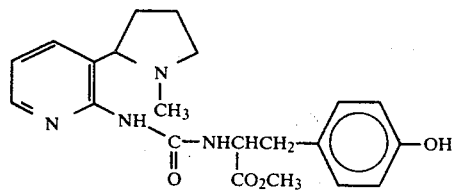

A mixture of 0.290 g of 2-aminonicotine and 0.500 g of methyl-2-isocyanato-3-(4'-trimethylsiloxyphenyl) propionate (made by the method of Example 2) was dissolved in 5 ml of dry pyridine and allowed to stir at ambient temperature overnight.

The solvent was removed in vacuo at ambient temperature and methanol was then added and the reaction mixture allowed to stir for an additional 30 minutes. Methanol was then removed in vacuo and the crude reaction product was crystallized from acetone to give the subject compound as a solid, mp 205°–6° C. (dec.).

This compound exhibited an $R_f$ of 0.77 when subjected to thin layer chromatography on silica gel using a 15% methanol-methylene chloride solvent system.

The ultraviolet absorption spectrum in 0.1 N NaOH displayed maxima at 286 nm (ε6,440) and 237 nm (ε21,800). The infrared spectrum of this compound (KBr) was characterized by bands at 3.3, 3.5, 5.75 (CO$_2$CH$_3$), 6.08, 6.32, 6.52, 6.97, 4.45, 8.30, 11.94, 12.45 and 12.90μ. The nmr spectrum in DMSO-d$_6$ was characterized by signals at δ10.32 (s, 1, NH), 9.70 (board d, 1, $J$=8.0 Hz, NH-CHCH$_2$), 9.23 (s, 1, —OH), 8.00 (d, 1, $J$=4.9 Hz, 6-proton), 7.55 (d, 1, $J$=7.0 Hz, 4-proton), 7.01 and 6.68 (A$_2$B$_2$q, 4, $J$=8.1 Hz, tyrosine 3'-, 5'- and 2'-,6'-protons respectively), 6.91 (m, 1, 5-proton), 4.50 (m, 1, tyrosine CH—CH$_2$), 3.64 (s, 3, CO$_2$CH$_3$), 2.95 (m, 2, tyrosine CHCH$_2$) and 2.13 ppm (s, 3, N—CH$_3$).

EXAMPLE 23

This Example shows the use of the present invention in the assaying of digoxin levels in blood serum by radioimmunoassay techniques.

Digoxin standards and unknowns were permitted to compete in separate sample wells with monoiodinated 15'-(TME) carbamyldigoxin-$^{125}$I (digoxin-$^{125}$I), produced as set forth in Example 6, for the limited number of binding sites in digoxin antiserum produced in rabbits. After incubation, the reaction mixture was transferred onto Sephadex G-25, fine, columns (Pharmacia Fine Chemicals Company), where separation of complexed digoxin from free digoxin was effected. The immunoreactions may be shown in equilibrium as follows:

digoxin-$^{125}$I + serum
   digoxin + anti-digoxin⇌(anti-digoxin.digoxin-$^{125}$I) + (anti-digoxin.serum
   digoxin) + digoxin-$^{125}$I + digoxin The incubate mixture formed above was placed onto the Sephadex G-25 column, and a 1.7 ml portion of eluant was applied so that the labeled and unlabeled antigens were absorbed and the labeled and unlabeled complexes were eluted, with the following results:

In the eluant: (anti-digoxin digoxin-$^{125}$I) + (anti-digoxin.digoxin)
On the column: digoxin-$^{125}$I + digoxin A prototype pipettor carousel and prototype centrifugal automated analyzer laboratory system were used in the following detailed procedure. A digoxin stock solution was prepared by dissolving 0.010 g of digoxin in 50 ml of 95% ethanol. One ml aliquots were stored frozen. An intermediate standard was obtained by diluting one ml of stock digoxin solution to 100 ml with a phosphate buffer solution. The phosphate buffer solution was prepared by dissolving 1.392 g of dipotassium hydrogen phosphate, 0.276 g of sodium dihydrogen phosphate and 8.76 g of sodium chloride in 750 ml of distilled-deionized water, adjusting the pH to 7.4 and then diluting up to 800 ml with distilled-deionized water. The intermediate standard contained 2.0 μg/ml. A working standard, prepared by adding 100 μl of intermediate standard to 9.9 ml of the phosphate buffer contained 20 ng/ml. The stock solution and intermediate solution may by kept frozen until use. Standards were made up to contain 20.0, 10.0, 5.0, 3.0, 2.0, 1.0, 0.4 and 0.0 ng/ml. A 250 μl supply of standards and unknowns were placed in the 0.5 ml sample cups which were than placed in the pipettor carousel.

A stock solution of antiserum was made by diluting 0.5 ml of 1:2300 titer rabbit antiserum to 10.0 ml with a 2% bovine serum albumin (BSA)/phosphate buffered saline (PBS) buffer solution.

The final working dilution (titer) was thus 1:46,000, of which 200 μl was used per smaple. Reagent boats (15 ml) for supplying the pipettor were positioned in the pipettor and loaded with antiserum reagent (10 ml), digoxin-$^{125}$I (2 ml) prepared as set forth in Example 6, and PBS wash (5 ml). The sample volume was dialed to deliver 50 μl. The sample plus wash volume was dialed to deliver 99 μl (50 μl sample plus 49 μl PBS wash). The pipettor was set to deliver 200 μl of antiserum reagent and 50 μl of radioactive antigen, digoxin-$^{125}$I. A 30 sample transfer disc was placed in the center of the carousel. While the transfer disc was being loaded by the pipettor, 30 test tubes (15×125 mm, Kimble 45042) were loaded into the test tube ring of the incubator/separator and a sufficient number of Sephadex G-25 columns were placed in the test tubes to equal the number of standards and unknowns (usually run in duplicate) being run. The system was primed with PBS buffer, the incubator was set for 15 minutes incubation, and the elution volume was set for 1.7 ml.

When the pipettor had finished its cycle of delivering antiserum, standards, unknown, and radioactive digoxin-$^{125}$I to the inner and outer compartments of the transfer disc, the latter was removed to the incubator/separator with care to retain the various solutions in their respective wells. The incubator/separator was switched on and allowed to operate for about 16 minutes, 15 minutes for incubation and one minute for elution through the Sephadex columns. The rotation during incubation was about 100 rpm, transferring the 200 μl of antiserum from its individual inner portion of the transfer disc into the individual outer portion of the transfer disc, where the 50 μl of unknown or standard antigen solution had been placed by the pipettor. After 15 minutes of incubation, the rotation was increased to 200 rpm for elution and rinsing. The unreacted antibody, serum and antigen-antibody complex were washed through the fine beads of the polystyrene-based Sephadex beads and into the bottom of the test tubes, while the labeled and unlabeled free antigen were slowed down by diffusion into the pores of the beads and remain on the columns.

A scintillation counter which counts three of the 30 positions at a time for one minute, so constructed that only the eluate bottom portion of the test tubes fits into the counter, was then used to count all smaples. Sequential counting of the 30 tubes thus required about 12 minutes. A small computer with printout capability then printed out the data after completion of the cycling through the 30 positions (ten times, three at a time). The printout in effect gave a dose-response curve for the batch of antiserum, since normally 18 of the 30 positions were filled with standards and 12 were filled with unknowns. Typically, four to six unknowns were run in duplicate. A mean value of 1.4±0.4 ng/ml with a range of from 0.8 to 2.4 ng/ml of digoxin has been found for non-toxic patients. A mean value for toxic patients has been found to be 3.3±1.5 ng/ml with a range of 2.1 to 8.7 ng/ml.

A typical standard curve is shown in the sole FIGURE. As can be seen, the present invention provides more than adequate sensitivity.

EXAMPLE 24

This Example demonstrates the use of the derivatives of the present invention in the assaying of cortisol levels in blood serum using radioimmunoassay techniques.

Cortisol levels in 0.2 ml of serum were determined after pretreatment by extracting the cortisol from non-specific binding proteins by 0.8 ml of 11% methanol in 0.05M barbital buffer at pH 8.6 and heating at 60° C. for 30 minutes. The same equipment and the same eluting columns were used as in Example 23, but the eluant volume was decreased to 1.4 ml. Other reagents used were a gelating barbital buffer consisting of 0.1% gelating in 0.05M sodium barbital buffer; cortisol; cortisol antiserum from sheep (S-114) diluted 1:16,000 in 0.1% gelatin barbital buffer, pH 8.6, 0.05M. the working standard of cortisol was 16 ng/50 μl. The antiserum and sample volumes were again 200 μl and 50 μl. The incubation time was increased to 30 minutes and the separation time to 1.5 minutes. A sample of 21-(TME)carbamylcortisol-$^{125}$I radiolabel (1.5 μCi/0.5 ml in ethanol) was diluted with 0.1% gelatin barbital buffer to give 18-20,000 cpm. This marker was found to give a 50:50 bound/free ratio at a further dilution of 1.10, that is, about 1,800 cpm under assay conditions.

In the same manner, a 21-(tyramine)carbamylcortisol-$^{125}$I radiomarker was found to give a 1:2 bound/free ratio in 895 counts per minute.

What is claimed is:

1. Isocyanates having the structural formaula:

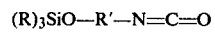

wherein R is a member selected from the group consisting of lower alkyl, alicyclics, aryl, alkaryl and aralkyl, each having no more than about 10 carbon atoms and R' is a radical selected from the group consisting of

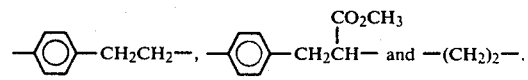

2. The isocyanates of claim 1 wherein R' is

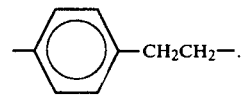

3. The isocyanates of claim 1 wherein R' is

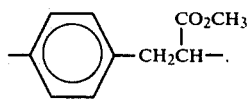

4. The isocyanates of claim 1 wherein R' is —(CH$_2$)$_2$—.

* * * * *